US010058399B2

(12) United States Patent
Katto (10) Patent No.: US 10,058,399 B2
(45) Date of Patent: Aug. 28, 2018

(54) DRILLS FOR DENTISTRY

(71) Applicant: TOSA ENTERPRISE CO., LTD., Tokyo (JP)

(72) Inventor: Akinori Katto, Tokyo (JP)

(73) Assignee: TOSA ENTERPRISE CO., LTD., Tokyo (JP)

( * ) Notice: Subject to any disclaimer, the term of this patent is extended or adjusted under 35 U.S.C. 154(b) by 134 days.

(21) Appl. No.: 15/137,077

(22) Filed: Apr. 25, 2016

(65) Prior Publication Data

US 2016/0317247 A1    Nov. 3, 2016

(30) Foreign Application Priority Data

Apr. 30, 2015  (JP) .................................. 2015-92695

(51) Int. Cl.
| | | |
|---|---|---|
| *A61C 1/08* | (2006.01) | |
| *A61C 8/00* | (2006.01) | |
| *A61C 1/05* | (2006.01) | |

(52) U.S. Cl.
CPC .............. *A61C 1/085* (2013.01); *A61C 1/05* (2013.01); *A61C 1/084* (2013.01); *A61C 8/0089* (2013.01); *A61C 8/001* (2013.01)

(58) Field of Classification Search
CPC ......... A61C 1/0585; A61C 1/05; A61C 1/084; A61C 8/001; A61C 8/0089

(Continued)

(56) References Cited

U.S. PATENT DOCUMENTS 1,321,130 A * 11/1919 Schlueter ............... A61C 1/082
433/76
1,380,040 A * 5/1921 Chayes ............... A61C 19/055
433/76

(Continued)

FOREIGN PATENT DOCUMENTS

| JP | 11-318940 | 11/1999 |
| JP | 2011-183157 | 9/2011 |

*Primary Examiner* — Nicholas Lucchesi
*Assistant Examiner* — Shannel Wright
(74) *Attorney, Agent, or Firm* — Wenderoth, Lind & Ponack, L.L.P.

(57) ABSTRACT

Drills for dentistry, which, in a dental implant treatment, enables two or more holes to be bored at a predetermined angle and interval in a minute space in which a single tooth grows and enables treatment to be performed precisely and rapidly regardless of a skill level of a dentist, wherein an arrangement is provided where a first member provided with a drill body and a second member provided with a fixing needle intersect slid-ably at a predetermined angle, the drill body is installed in a direction perpendicular to an axial direction of the first member with its tip facing a direction in which the fixing needle is provided, the fixing needle is installed in a direction perpendicular to an axial direction of the second member with its tip facing a direction in which the drill body is provided, the drill body bores a first hole, bored obliquely with respect to a natural tooth growing direction, and a second hole facing the first hole mutually at a predetermined angle, and the second hole is bored by the drill body upon inserting the fixing needle in the first hole, fixing the second member to the jawbone, and sliding the first member with respect to the second member, fixed to the jawbone, as a reference.

7 Claims, 9 Drawing Sheets

(58) Field of Classification Search
USPC .............................................. 606/80, 96, 102
See application file for complete search history.

(56) References Cited

U.S. PATENT DOCUMENTS

| | | | | |
|---|---|---|---|---|
| 2,744,327 A | * | 5/1956 | Birnbaum | A61C 1/085 |
| | | | | 433/116 |
| 3,037,282 A | * | 6/1962 | Aktarian | A61C 1/085 |
| | | | | 433/128 |
| 3,895,444 A | * | 7/1975 | Small | A61C 1/084 |
| | | | | 433/174 |
| 4,344,755 A | * | 8/1982 | Gold | A61C 19/055 |
| | | | | 433/76 |
| 5,222,892 A | * | 6/1993 | Perry | A61C 1/084 |
| | | | | 433/50 |
| 5,306,148 A | * | 4/1994 | Nakamura | A61C 5/90 |
| | | | | 433/116 |
| 5,688,283 A | * | 11/1997 | Knapp | A61C 1/084 |
| | | | | 433/75 |
| 5,741,133 A | * | 4/1998 | Gordils | A61C 1/084 |
| | | | | 433/76 |
| 6,926,525 B1 | | 8/2005 | Ronvig et al. | |
| 2004/0043355 A1 | * | 3/2004 | Jonsson | A61C 1/082 |
| | | | | 433/75 |
| 2005/0069835 A1 | * | 3/2005 | Bompard | A61C 1/084 |
| | | | | 433/76 |
| 2011/0217668 A1 | * | 9/2011 | Hung | A61C 1/085 |
| | | | | 433/76 |
| 2016/0331489 A1 | * | 11/2016 | Sanders | A61C 1/082 |

* cited by examiner

PRIOR ART

DRILLS FOR DENTISTRY

FIELD OF THE INVENTION

The present invention relates to drills for dentistry and specifically relates to drills for dentistry for boring a hole in a jawbone during dental implant treatment.

BACKGROUND OF THE INVENTION

Dental implant treatment, performed upon loss of a natural tooth and by implanting an artificial tooth root (implant body) in the jawbone at the location of tooth loss and using the artificial tooth root as a base to mount an artificial tooth thereon, has been conventionally known.

With the dental implant treatment that is currently being practiced, after surgically excising the gums above the jawbone (alveolar bone), an implant body of a size determined beforehand by examination is implanted in the jawbone and thereafter, there is a necessary waiting period of of three months to six months for integration (osseointegration) of the implant body and the jawbone. Treatment is then performed through the procedures of mounting a pedestal, referred to as an "abutment body," on the implant body that has integrated with the jawbone and mounting an artificial tooth that has been molded to a predetermined size in advance on the abutment body.

The dental implant treatment is performed in accordance with these procedures and therefore six months to one year are generally required as a treatment period.

Also, depending on the patient, the bone amount (especially the bone thickness) required for implanting the implant body may be insufficient, especially in the case of performing treatment on the maxilla. In this case, first, an auxiliary operation, such as a guided bone regeneration method (GBR method), ridge expansion, socket lifting, sinus lifting, etc., is performed on the jawbone and the dental implant treatment is performed upon forming the necessary bone amount, thus requiring an additional treatment period of several months.

Conventionally-known dental implant treatments, such as those mentioned above, require a long treatment period and therefore had the problems that, for a patient, the treatment methods cannot be said to be available to everyone due to the high time and economic burdens and, even if treatment can be received, the mental and physical burdens were high due to inconvenience being imposed over a long period.

In view of such problems of the conventional dental implant treatments, the present applicant proposed the following art in a prior application (Japanese Patent Application No. 2014-109085).

Figure 11:
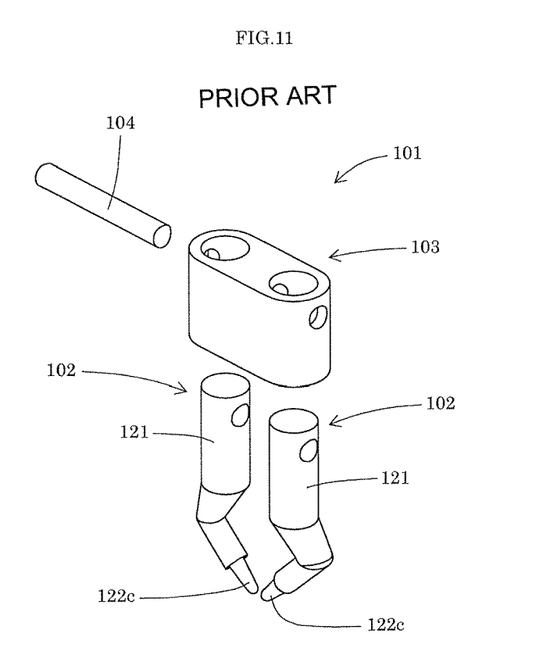
FIG. 11 is a schematic perspective view of an embodiment of a dental implant system according to a prior application by the present applicant.
Figure 12:
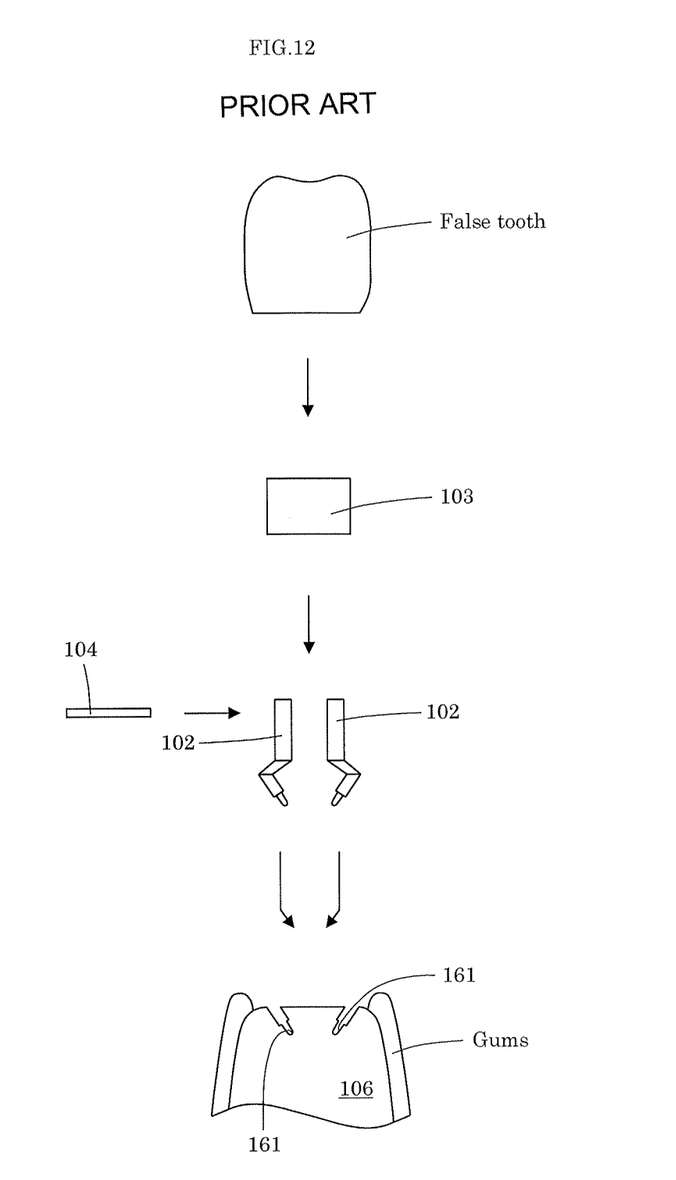
FIG. 12 is an exploded arrangement diagram for describing the dental implant system shown in FIG. 11.

As shown in FIG. 11 and FIG. 12, the prior proposed art is a dental implant system 101 with an arrangement where at least two implant bodies 102, each having a shaft portion 121, form a pair, a hook portion 122, hooked in a hook hole 161 bored in a jawbone 106, is provided on the shaft portion 121 of each implant body 102, the hook portion 122 is bent with respect to the shaft portion 121, and when the respective implant bodies 102 are hooked onto the jawbone 106, tip portions 122c of the hook portions 122 are positioned so as to face each other inwardly, the arrangement being provided with a fixing means for fixing the implant bodies 102 to each other.

With the invention according to the prior application by the present applicant, by simply hooking the implant bodies 102 onto the jawbone 106 and using an abutment body 103 and a fixing member 104 to integrally integrate the respective implant bodies 102, the integrally integrated implant bodies 102 are fixed to the jawbone 106, and therefore a period for integration of the implant bodies and the jawbone is not required as in the conventional implant treatment, and the treatment period and the number of times of treatment can be reduced. Treatment of a patient whose jawbone is small in bone amount or thickness is also enabled and elongation of the treatment period due to an auxiliary operation can also be avoided. That is, the dental implant system according to the prior application differs fundamentally from the conventional implant treatment in which the implant bodies are fused to the jawbone, and enables firm fixing to be achieved by a mode of clamping the jawbone by two implant bodies while reducing the treatment period and the number of times of treatment of many patients regardless of the bone amount of the jawbone, etc., and minimizing the impact to the jawbone to lighten the mental and physical burdens of the patients.

As mentioned above, with the dental implant system 101 according to the prior application, the at least two hook holes 161, bored in the jawbone 106 at the location to be treated, must be bored at a predetermined interval and in directions of facing each other inwardly (at a predetermined angle).

However, there is a problem that using a conventionally used dental drill, it is extremely difficult to bore two or more holes (hook holes) at a predetermined angle and interval in a minute space in which a single tooth grows, and reliability of treatment cannot be secured.

The following arts have been proposed as arts used in dental treatment to bore a hole at a precise position.

The art described in Patent Document 1 (Japan Patent Pre-Publication No. H11-318940) is an art relating to:

"A parallel cutting aiding tool for dentistry arranged from a mounting portion (1), equipped with one of either a shaft or bearing that is a member constituting a first coupling joint (A) for rotatingly actuating a shaft when the shaft is mounted adjacent an external front surface (outer side of dental arch) or rear surface (inner side of dental arch) of a substantially central portion of a groove (1a) of a shape having a depth and width that are in accordance with a predetermined location of a dental arch, and an arm portion constituted of a first arm (2), equipped at one end with a bearing or shaft that is a remaining member constituting the first coupling joint (A) and equipped at another end with one of either a shaft or bearing that is a member constituting a second coupling joint (B) having a rotational axis parallel to an axis of the first coupling joint (A) and being for rotatingly actuating a shaft when the shaft is mounted, and a second arm (3), equipped at one end with a bearing or shaft that is a remaining member constituting the second coupling joint (B) and equipped at another end with a hand piece mounting portion (5) for detachably attaching a hand piece, and being arranged so that when a hand piece (6) is mounted on the hand piece mounting portion (5), an angle (θ) formed by a rotational center line of a cutting tool (6a) mounted on the hand piece (6) and the axis of the first coupling joint (A) is set to a desired angle (symbols are those in Patent Document 1)."

The art described in Patent Document 2 (Japan Patent Pre-Publication No. 2011-183157) is an art relating to:

"A positioning aiding apparatus for boring a plurality of dental implant holes, the apparatus including a main arm unit including an arm body having a first end and a second end disposed to face each other and having a reference shaft pivoting above the first end, a first connecting head pivoting at the second end of the main arm unit via a connecting shaft and pivoting in all sequences, and an extension arm unit having a pair of connecting rods, a second connecting head, a drill guide portion disposed above an outer end portion of the second connecting head, the drill guide portion having a drill guide hole.

However, although these arts enable a hole having a predetermined angle to be bored at a position of predetermined distance or interval with respect to a certain location within an oral cavity as a reference, as the interval between the reference part and the location at which the hole is bored, for example, only an interval such as that from a back tooth at the left side to a back tooth at the right side is presumed, and there is a problem that boring of two or more holes at a predetermined angle and interval in a minute space in which a single tooth grows as in the art according to the prior application by the present applicant is not enabled.

Dental drills and positioning aiding apparatuses for dentistry that have already been proposed thus cannot be applied to the art according to the prior application by the present applicant.

Patent Document 1: Japan Patent Pre-Publication No. H11-318940

Patent Document 2: Japan Patent Pre-Publication No. 2011-183157

SUMMARY OF THE INVENTION

Therefore, an object of the present invention is to provide a dental drill that enables two or more holes to be bored at a predetermined angle and interval in a minute space in a jawbone in which a single tooth grows and enables treatment to be performed precisely and rapidly regardless of a skill level of a dentist.

The object of the present invention is achieved by the following arrangements.

1. Drills for dentistry for boring a hole in a jawbone, the dental drill including a first member and a second member and having an arrangement where the first member and the second member intersect slid-ably at a predetermined angle,
a drill body for boring a hole in a jawbone is provided at one end of the first member,
a fixing needle for insertion into the hole bored in the jawbone is provided at one end of the second member,
the drill body is installed in a direction perpendicular to an axial direction of the first member with a tip of the drill body facing a direction in which the fixing needle is provided,
the fixing needle is installed in a direction perpendicular to an axial direction of the second member and arranged with a tip of the fixing needle facing a direction in which the drill body is provided,
the drill body bores a first hole, bored obliquely with respect to a natural tooth growing direction, and a second hole facing the first hole mutually at a predetermined angle,
the second hole is bored by the drill body upon inserting the fixing needle in the first hole, fixing the second member to the jawbone, and sliding the first member with respect to the second member, fixed to the jawbone, as a reference, and
a plurality of holes are bored in boring directions facing each other at a predetermined angle with respect to the natural tooth growing direction as a reference.

2. The dental drill according to the above 1 with an arrangement where the first hole is bored obliquely from an inner side toward an outer side or from the outer side to the inner side of a tooth row, and the second hole is bored obliquely and oppositely of the first hole from the outer side toward the inner side or from the inner side to the outer side of the tooth row.

3. The dental drill according to the above 1 or 2 with an arrangement where the first member is provided with a gear (pinion) and an operating portion coupled to the gear,
an axial direction side surface of the second member is provided with a rectilinear cog rail (rack), and
when the gear is rotated by rotating the operating portion, the gear and the rectilinear cog rail are engaged and the first member and the second member slide rectilinearly.

4. The dental drill according to the above 3 where the rectilinear cog rail (rack) provided on the second member has a stopper provided at an end portion at the side at which the fixing needle is provided.

5. The dental drill according to any one of the above 1 to 4 where with each of the drill body and the fixing needle, a step portion is provided between a tip portion and another portion and the tip portion is smaller in diameter than the other portion.

6. The dental drill according to any one of the above 1 to 5 where the first member is provided with a single drill body and
the second member is provided with a single fixing needle.

7. The dental drill according to any one of the above 1 to 5 where the first member has two drill bodies provided in parallel at a predetermined interval, and
the second member has two fixing needles provided in parallel at the same interval as the two drill bodies.

8. The dental drill according to any one of the above 1 to 7 where the drill body of the first member has an air turbine structure, and
the first member is provided with an air flow passage connecting the drill member and an air supply source and provided with an air regulating valve restricting a flow of air in the air flow passage.

With the invention according to the above 1, by first boring the first hole obliquely with respect to the natural tooth growing direction in the jawbone by the drill body provided on the first member,
inserting the fixing needle, provided on the second member, into the bored first hole to fix the second member to the jawbone, and
then sliding the first member with respect to the second member, fixed to the jawbone, as a reference and boring the second hole in the jawbone by the drill body,
a plurality of holes, having a predetermined interval and with which the boring directions face each other at a predetermined angle, can be bored.

Also with the invention according to the above 1, the angle at which the first hole and the second hole are bored is restricted by the angle at which the first member and the second member intersect, the interval between the positions at which the first hole and the second hole are bored is restricted by the lengths of the first member and the second member, and therefore a plurality of holes having a predetermined interval and with which the boring directions face each other at a predetermined angle can be bored precisely and rapidly regardless of a skill level of a dentist.

With the invention according to the above 2, as a means of use of the dental drill according to the above 1, an arrangement is provided where the first hole is bored obliquely from the inner side toward the outer side or from the outer side to the inner side of the tooth row, and the second hole is bored obliquely and oppositely of the first hole from the outer side toward the inner side or from the inner side to the outer side of the tooth row, thereby enabling treatment even at a location sandwiched by teeth at the front and rear and enabling mounting of the dental implant according to the prior application in a mode of clamping the jawbone from the inner side and the outer side.

With the invention according to the above 3, the first member and the second member are made slid-able by a combination of the gear (pinion) and the rectilinear cog rail (rack). That is, by rotating the operating portion, the rotational force is converted rectilinearly to enable the first member and the second member to slide rectilinearly. Actuation due to the sliding can thereby be controlled finely to enable the work of boring into the jawbone by the drill body to be made precise and rapid.

With the invention according to the above 4, the stopper is provided at the end portion of the rectilinear cog rail (rack) provided on the second member, and movement of the first member with respect to the second member as a reference is thereby restricted to enable the drill body to be controlled so as not to cut the jawbone too deeply.

With the invention according to the above 5, by providing each of the drill body and the fixing needle with the wide/narrow, two-step arrangement with the step portion being provided between the tip portion and the other portion and the tip portion being made smaller in diameter than the other portion, the depth of insertion of the fixing needle into the hole bored in the jawbone by the drill body can be made fixed. In detail, the hole bored by the drill body is bored to have diameters of the two steps of wide and narrow and when the fixing needle is inserted into the hole, the entry of the fixing needle into the hole is stopped by contact of the step difference portion of the hole and the step portion of the fixing needle and the depth of insertion of the fixing needle into the hole can be made fixed.

With the invention according to the above 6, the arrangement is such that one each of the drill body and the fixing needle are provided and at least two holes, with which the boring directions face each other at a predetermined angle, can be bored.

With the invention according to the above 7, the arrangement is such that two each of the drill bodies and the fixing needles are provided and four holes, with which the boring directions face each other at predetermined angles, can be bored in a single series of processes.

Also, the interval between two holes can be maintained precisely because the two drill bodies are aligned in parallel at the predetermined interval.

Yet further, the fixing needles can be inserted in the two holes respectively so that the jawbone and the second member are fixed at two points, and fixing of the two can thus be made firmer.

With the invention according to the above 8, when the drill body is made to have the air turbine structure, the air flow passage provided in the first member can be controlled to open and close by means of the air regulating valve. With this arrangement, when the air flow passage is opened widely by means of the air regulating valve, the amount of air passing therethrough is increased so that the drill body is rotated at a high speed, and oppositely when the air flow passage is opened narrowly, the amount of air passing therethrough is decreased to enable the drill body to be rotated at a low speed. If the drill body rotates at a high speed, a hard jawbone can be cut rapidly, and on the other hand, if the drill body rotates at a low speed, the jawbone can be cut a little at a time carefully so that the jawbone is not broken by the cutting.

A dental drill 1 according to the present invention is a dental drill used for dental implant treatment and is a dental drill used to bore a plurality of holes, having a predetermined interval and with which boring directions face each other at a predetermined angle, in a jawbone.

The present invention shall now be described in detail in accordance with the attached drawings.

Figure 1:
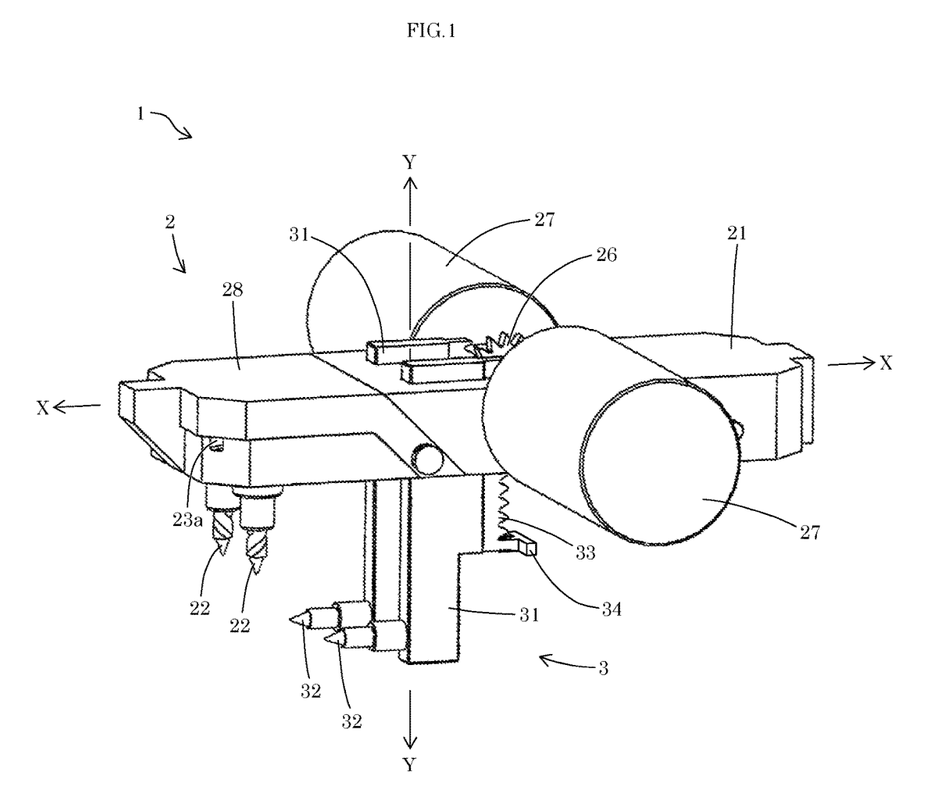
FIG. 1 is a perspective view of an embodiment of drills for dentistry of the present invention.
Figure 2:
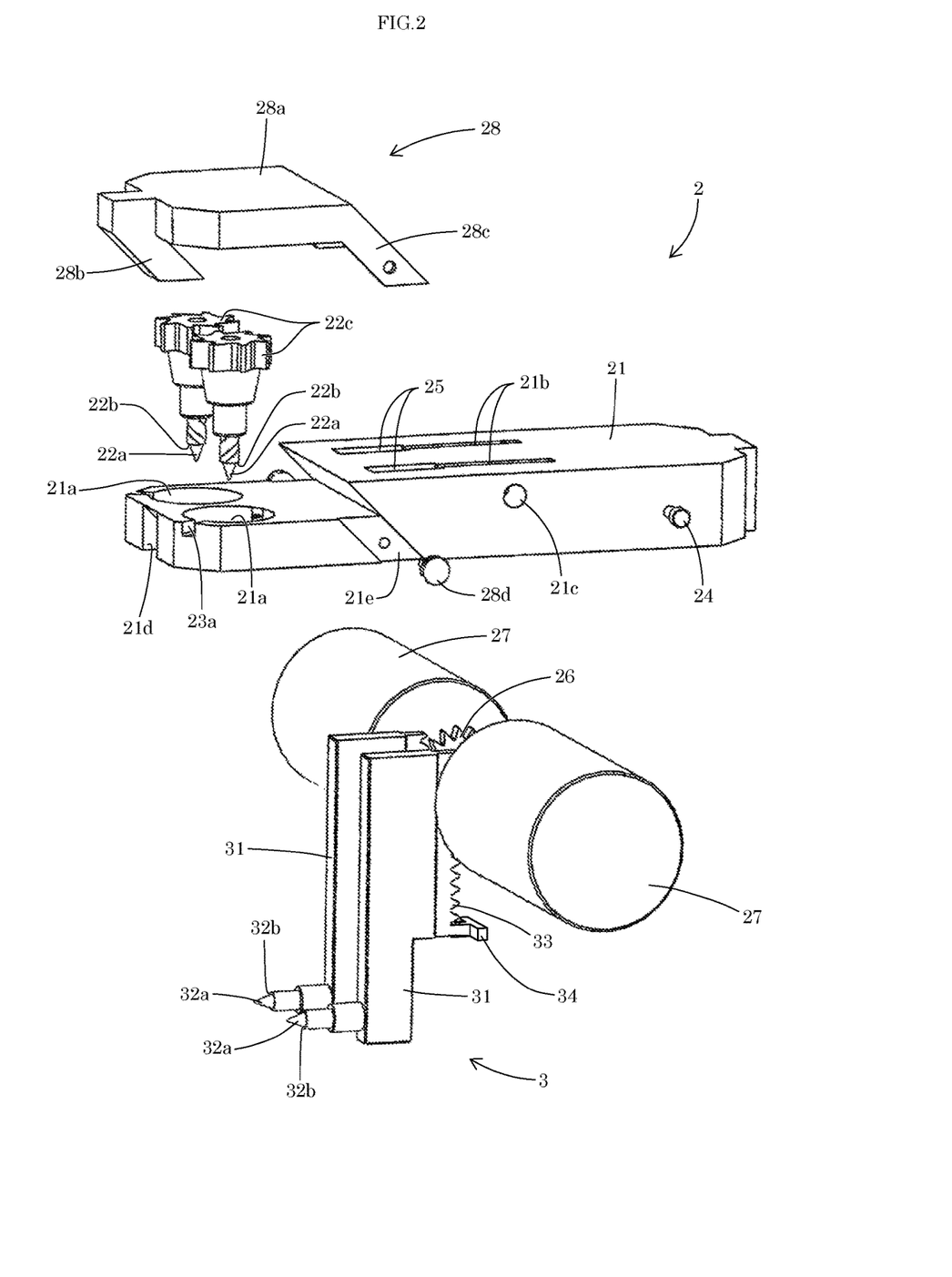
FIG. 2 is an exploded perspective view of the drills shown in FIG. 1.
Figure 3:
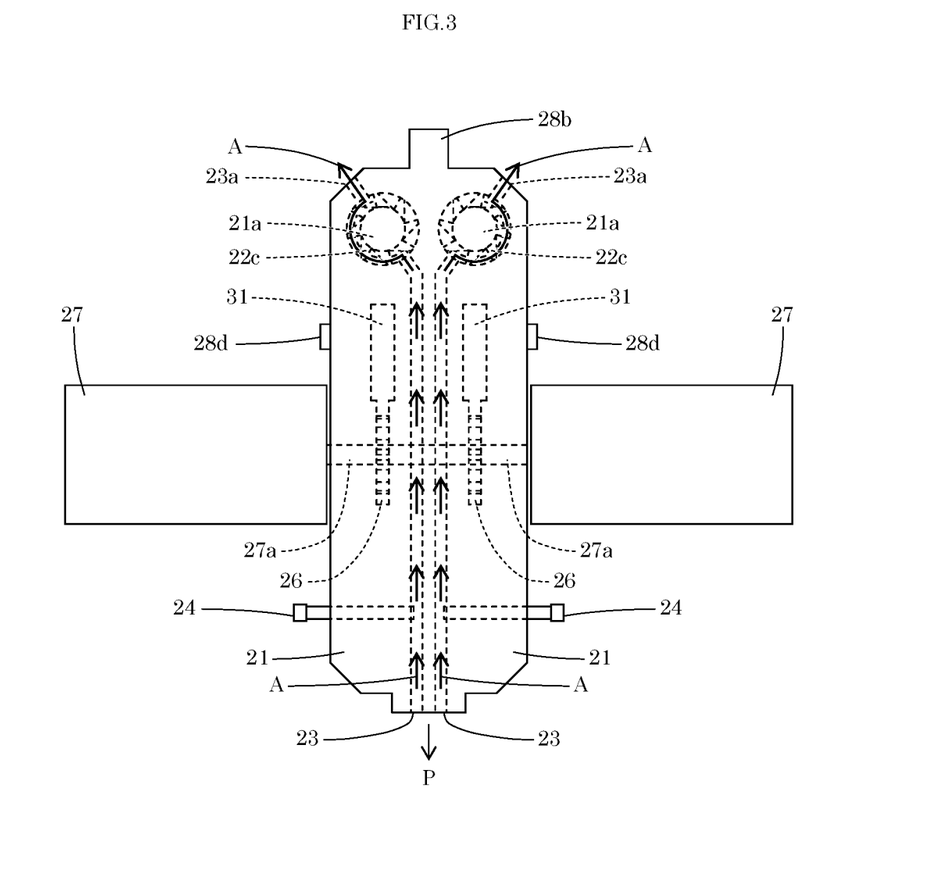
FIG. 3 is a schematic plan view of the internal arrangement of the drills shown in FIG. 1.
Figure 4:
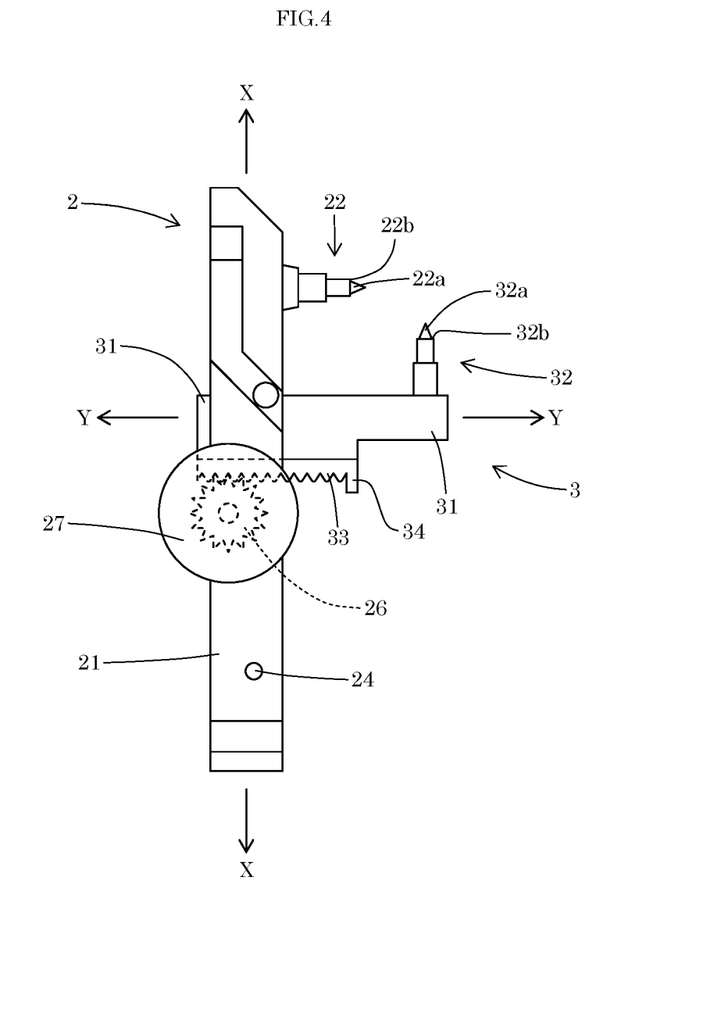
FIG. 4 is a schematic side view of a portion of the internal arrangement of the dental drill shown in FIG. 1.

FIG. 1 is a perspective view of an embodiment of the drills 1 according to the present invention (may hereinafter be referred to simply as "the dental drill"). FIG. 2 is an exploded perspective view of the dental drill 1 shown in FIG. 1. FIG. 3 is a schematic plan view of the internal arrangement of the drills 1 shown in FIG. 1. FIG. 4 is a schematic side view of a portion of the internal arrangement of the dental drill 1 shown in FIG. 1. In FIG. 3 and FIG. 4, the internal arrangement that does not appear in the outer appearance is indicated by broken lines. There are also portions of the internal arrangement that are omitted and unillustrated.

As shown in FIGS. 1 to 2, the drills 1 is arranged from a first member 2 and a second member 3 that intersect at a predetermined angle and are slid-ably mounted.

First, the first member 2 shall be described.

As shown in FIGS. 1 to 4, the first member 2 is arranged from at least a rod-shaped base portion 21 and drill bodies 22 and may be provided with air flow passages 23, air regulating valves 24, insertion holes 25, gears 26, operating portions 27, a drill fixing portion 28, etc.

The drill bodies 22 are provided at one end of the base portion 21 of the first member 2. The mounting direction is a direction perpendicular to an axial direction (longitudinal direction) X of the base portion 21 and tip portions 22a of the drill bodies 22 are made to face a direction in which fixing needles 32 of the second member 3 to be described below are provided.

As each drill body 22, a well known and used drill body, used as a drill, cutting tool, or boring tool for dentistry, may be adopted without any restrictions in particular.

Each drill body 22 is preferably an extra-fine member with a sharp tip, similar to an injection needle. For example, the drill body preferably has a diameter of not more than 3 mm and more preferably has a diameter of not more than 2 mm. By thus forming the drill body 22 as an extra-fine member, it becomes possible to make the drill body 22 pierce from above a gum 5 and make it penetrate to the jawbone 4 and cut the jawbone 4 from there. In this case, a step of cutting the gum 5 to expose the jawbone 4, which is performed in an ordinary implant treatment, may be omitted.

Preferably as shown in FIGS. 1, 2, and 4, each drill body 22 has a step portion 22b provided between the tip portion 22a and another portion and the tip portion 22a is smaller in diameter than the other portion. That is, the diameter of the drill body 22 preferably has a wide/narrow, two-step arrangement. By this arrangement, the depth of insertion of a fixing needle 32 (to be described below) into a hole 41 or 42 bored in the jawbone by the drill body 22 can be made fixed. In detail, the hole 41 or 42 bored by the drill body 22 is bored to have diameters of the two steps of wide and narrow and when the fixing needle 32 is inserted into the hole, the entry of the fixing needle 32 into the hole 41 or 42 is stopped by contact of the step difference portion of the hole and a step portion 32b of the fixing needle 32 and the depth of insertion can be made fixed.

As the structure of each drill body 22, it is preferable to adopt an air turbine structure. In this case, as shown in FIG. 2, the drill body 22 is provided with a rotary vane 22c at another end side of the tip portion 22a. With this arrangement, the rotary vane 22c is rotated by an air flow A and in coupled movement therewith, the entirety of the drill body 22, including a drill blade, is rotated. As the air turbine structure, a well known and used art in the field of dental drills may be adopted without any restrictions in particular.

The embodiment shown in FIG. 2, etc., has hollow drill body housing portions 21a provided in the base portion 21 of the first portion 2 and is arranged so that the drill bodies 22 are housed in the drill body housing portions 21a. In detail, with this arrangement, the rotary vane 22c of a drill body 22 is housed in each drill body housing portion 21a and the drill blade portion, including the tip portion 22a and the step portion 22b, projects through the base portion 21 and is exposed to the exterior.

Figure 5:
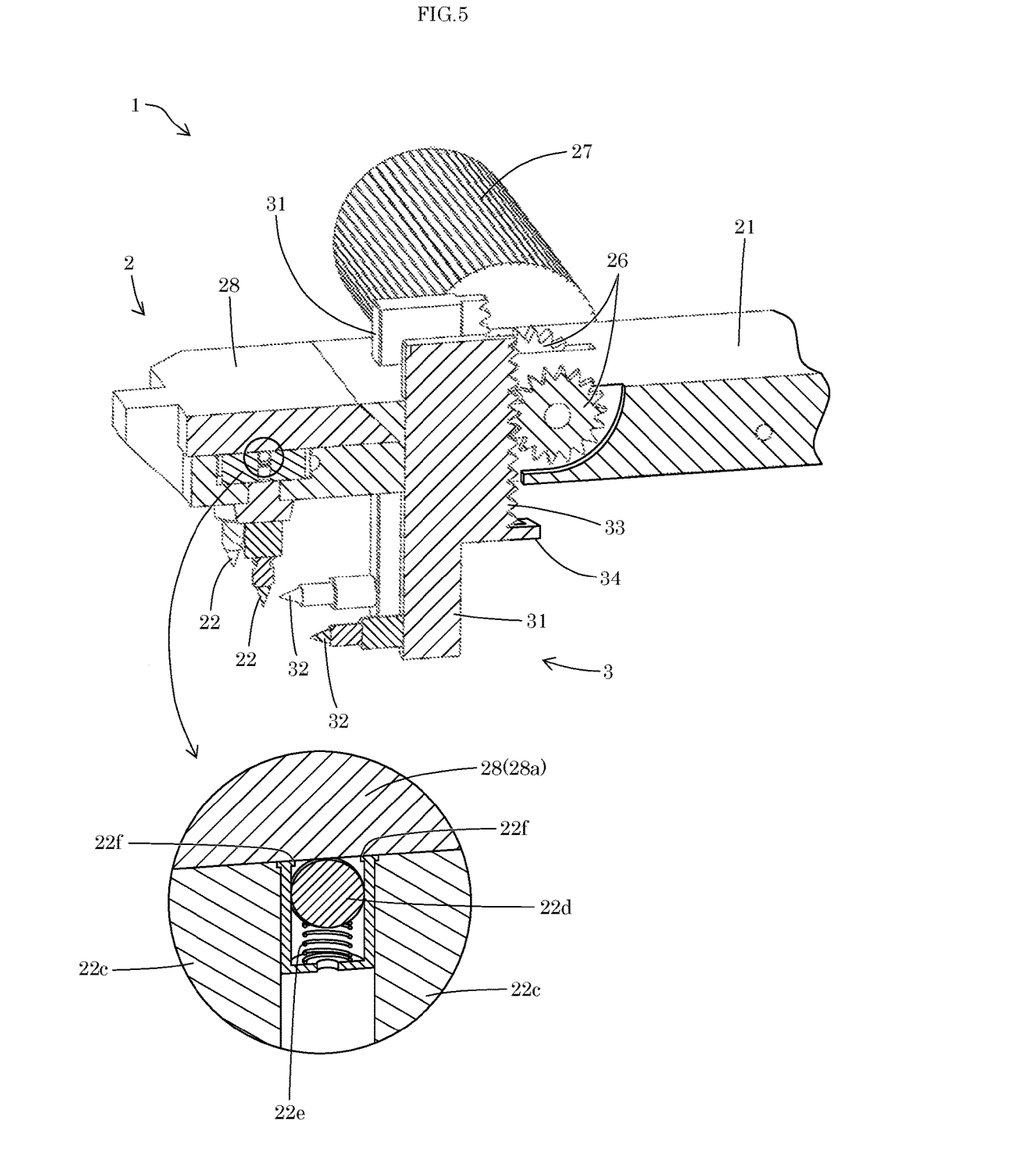
FIG. 5 is a schematic sectional view showing, in enlarged manner, a portion of a rotary vane of a drill body in the drills shown in FIG. 1.

FIG. 5 is a schematic sectional view showing, in enlarged manner, a portion of the rotary vane 22c of a drill body 22. As shown in FIG. 5, in the case where each drill body 22 has the air turbine structure, the rotary vane 22c is preferably provided with a bearing 22d. The bearing 22d is preferably provided on the axis of the drill body 22 at an upper surface of the rotary vane 22c and an arrangement where a hollow or recessed portion is provided at this position to house the bearing 22d is preferable. By thus providing the bearing 22d, the rotation of the drill body 22 is stabilized, axial wobbling is made unlikely to occur, and occurrence of wear and abnormal noise due to contact with the drill fixing portion 28 to be described below can be prevented. The drill fixing portion 28 to be described below may be provided with a hollow portion, etc., for receiving the bearing 22d at a position of contact with the bearing 22d.

As shown in FIG. 5, a spring 22e is preferably provided at a portion below the bearing 22d. The spring 22e is for pressing the bearing 22d upward, that is, in the direction of the drill fixing portion 28. By providing the spring 22e, the bearing 22d and the drill fixing portion 28 to be described below can be put in contact reliably.

The bearing 22d is pressed by the spring 22e and therefore a portion thereof projects further outward than the upper surface of the rotary vane 22c. When the drill fixing portion 28 is then mounted onto a predetermined position, the bearing 22d is put in a condition where it is pushed by the drill fixing portion 28 and returned in the direction of the spring 22e, and in this state, the rotary vane 22c and the drill fixing portion 28 are put in contact via the bearing 22d.

When the spring 22e is installed, the bearing 22d is pressed upward and may thus come off upwardly in a state where the drill fixing portion 28 is not mounted. It is therefore preferable to provide the hollow or recessed portion housing the bearing 22d with an overhanging portion 22f as shown in FIG. 5 as an arrangement for preventing the bearing 22d from coming off.

Figure 6:
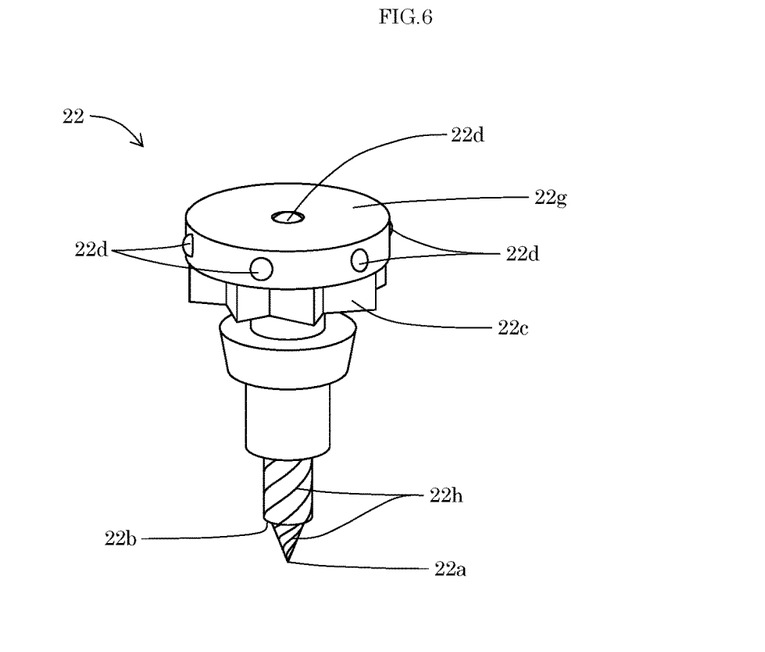
FIG. 6 is a perspective view of another embodiment of the drill body.

FIG. 6 shows another embodiment of the drill body 22.

The drill body 22 shown in FIG. 6 is provided with a disc portion 22g having a fixed thickness at a portion above the rotary vane 22c. A side surface of the disc portion 22g is provided with a plurality of bearings 22d. By this arrangement, occurrence of wear and abnormal noise due to friction can be prevented by the bearings 22d provided in the side surface even when the drill body 22 contacts a side wall of the drill body housing portion 21a. Although the number of bearings 22d provided in the side surface is not restricted, it is preferable to install three or more bearings 22d at equal intervals.

Even with the embodiment shown in FIG. 6, it is preferable to provide the bearing 22d on the axis of the above-described drill body 22. In this case, an arrangement is provided where the bearing 22d is provided at a center of an upper surface of the disc portion 22d and together with the bearings 22d provided in the side surface, occurrence of wear and abnormal noise due to contact of the drill body 22 with other portions can be prevented.

The parts of the embodiment shown in FIG. 6 capable of boring into the jawbone 4 are a sharp part, including the tip portion 22a, and a part provided with a helical groove and these parts are indicated as a drill blade 22h. A part besides these is a portion connecting the drill blade 22h and the rotary vane 22c and is not capable of boring into the jawbone 4. That is, by keeping the length of the drill blade 22h at approximately that shown in FIG. 6 and providing a step difference between the drill blade 22h and the portion besides it, excessively deep cutting of the jawbone 4 is prevented.

As shown in FIG. 3, the air flow passages 23 are provided in the base portion 21. The air flow A in each air flow passage 23 is arranged such that air from an air supply source P, such as an air pump, etc., flows in and passes through the drill body housing portion 21a and the air flows out through an exhaust hole 23a. The air flowing through the air flow passage 23 is arranged to make the rotary vane 22c rotate in the drill body housing portion 21a to make the entire drill body 22 rotate.

An air regulating valve 24 may be provided in each air flow passage 23. The air regulating valve 24 is for regulating an amount of air passing through the air flow passage 23 and has a structure that widens a cross-sectional area of the air flow passage 23 to increase the air passage rate and oppositely narrows the cross-sectional area of the air flow passage 23 to decrease the air passage rate.

By thus regulating the amount of air passing through the air flow passage 23, a rotational speed of the drill body 22 can be regulated. That is, when the flow rate of air is high, the drill rotates at a high speed and when the flow rate of air is low, the drill rotates at a low speed.

As the arrangement of the air regulating valve 24, an arrangement can be cited where, for example as shown in FIG. 3, a rod-shaped air regulating valve 24 is inserted from a side of the air flow passage 23 and a degree of opening (cross-sectional area) of the air flow passage is regulated by the depth of insertion. When the depth of insertion of the rod-shaped air regulating valve 24 is deep, the flow of air in the air flow passage 23 is obstructed and the flow rate of air is decreased, and when the depth of insertion is shallow, the flow of air in the air flow passage 23 is not obstructed and the flow rate of air is increased.

The base portion 21 may be provided with insertion holes 25 for intersectingly mounting the second member 3. As shown in FIG. 2, the insertion holes 25 are holes provided in the base portion 21 of the first member 2 for insertion of base portions 31 of the second member 3. Although two insertion holes 25 are provided in FIG. 2, this is because there are two of the base portions 31 of the second member 3, and in the present invention, there is no restriction in the number of insertion holes 25. Also, the shape of each insertion hole 25 is formed in correspondence to the shape of each base portion 31 of the second member 3.

The gears 26 may be provided at parts adjacent to the insertion holes 25. The gears 26 correspond to the rectilinear cog rails 33 provided on the second member 3 to be described below. Also, the gears 26 may be provided with the operating portions 27 for rotation thereof.

The embodiment shown in FIG. 2, etc., has an arrangement where gear installation holes 21b are provided adjacent the insertion holes 25 and the gears 26 are housed therein. Each operating portion 27 is provided with a shaft body 27a that is coaxial to a gear 26. The shaft body 27a is inserted into an operating portion installation hole 21c and put in communication with the gear 26 and is arranged so that when the operating portion 27 is rotated, the gear 26 also rotates.

By these arrangements, a rack-and-pinion structure is formed with the gears 26 as pinions and the rectilinear cog rails 33 as racks to enable the rotation of the gears to be converted to a rectilinear movement. That is, by the rack-and-pinion structure, a mechanism is arranged where the second member 3, provided with the cog rails (racks) 33 is made to slide vertically rectilinearly by the gears (pinions) 26 rotated by the operating portion 27. By adopting this arrangement, the vertical sliding can be controlled finely to enable a process of boring into the jawbone 4 by the drill bodies 22 to be performed precisely and rapidly.

Each drill body 22 has an arrangement that is detachable from the first member 2 and is replaceable. For sanitation reasons, it is preferable to replace the drill bodies 22 each time use is made on a different patient. As a means for mounting the drill bodies 22 detachably, an arrangement can be cited where, as shown in FIG. 2, etc., the base portion 21 is provided with the drill body housing portions 21a and the drill fixing portion 28 is provided for closing the open upper portions.

In the embodiment shown in FIGS. 1 and 2, the drill fixing portion 28 is arranged from a lid portion 28a, a tip leg portion 28b, side surface leg portions 28c, and fixing screws 28d. The present embodiment has an arrangement where the lid portion 28a is set so as to cover the rotary vanes 22c housed in the drill body housing portions 21a. The drill fixing portion 28 and the rotary vanes 22 may have an arrangement of being provided with minute gaps and not being put in contact so that the rotations of the drill bodies 22 are not obstructed. Also, the drill fixing portion 28 and the rotary vanes 22 may be arranged so as to be put in contact via the bearings 22d as described above. In this case, hollow portions, etc., for receiving bearings 22d may be provided at positions of the lid portion 28a of the drill fixing portion 28 that contact the bearings 22d.

The lid portion 28a is fixed to the base portion 21 by the tip leg portion 28b, the side surface leg portions 28c, and the fixing screws 28d so as not to fall off unexpectedly. That is, with the arrangement shown in FIGS. 1 and 2, unexpected falling-off of the lid portion 28a from the base portion 21 and detachment of the drill bodies 22 can be prevented by the tip leg portion 28b being inserted or loosely fitted in a tip recessed portion 21d provided at an end portion of the base portion 21, the side surface leg portions 28c provided at the right and left sides being inserted or loosely fitted in side surface recessed portions 21e provided at right and left side surfaces of the base portion 21, and the fixing screws 28d being mounted thereto.

The second member 3 shall now be described.

As shown in FIGS. 1, 2, and 4, the second member 3 is arranged from at least the rod-shaped base portions 31 and the fixing needles 32 and may be provided with the rectilinear cog rails 33 and stoppers 34.

The fixing needles 32 are members for insertion into the holes 41 and 42 bored in the jawbone 4 by the drill bodies 22. By insertion of the fixing needles 32 into the holes 41 and 42 bored in the jawbone 4, the second member 3 having the fixing needles 32 is fixed to the jawbone 4.

As shown in FIGS. 1, 2, and 4, each fixing needle 32 is installed in a direction perpendicular to an axial direction (longitudinal direction) Y of the second member 3 and a tip portion 32a of the fixing needle 32 is made to face the direction in which the drill bodies 22 are provided.

The fixing needles 32 have substantially the same shape as the drill bodies 22 of the first member 2.

As mentioned above, preferably, each drill body 22 has the step portion 22b provided between the tip portion 22a and the other portion and the tip portion 22a is smaller in diameter than the other portion. Therefore, in the case where each drill body 22 has the two-step diameter arrangement provided with the step portion 22b, each fixing needle 32 has an arrangement where the step portion 32b is provided between the tip portion 32a and another portion and the tip portion 32a is smaller in diameter than the other portion. That is, the diameter of the fixing needle 32 preferably has a wide/narrow, two-step arrangement.

Each fixing needle 32 is preferably detachable from the second member 3. Even when a drill body 22 is changed to one of different size, replacement with a fixing needle 32 of substantially the same size is thereby enabled. Also in consideration of sanitation aspects, it is preferable to replace the fixing needles 32 each time use is made on a different patient. A detachment/attachment means for replacement is not restricted and a well known and used arranged may be adopted without any restrictions in particular.

The rectilinear cog rails 33 may be provided on the side surfaces of the base portions 31 of the second member 3. The rectilinear cog rails 33 correspond to the gears 26 provided on the first member 2 described above, and when the gears 26 are rotated by the operating portions 27, the rectilinear cog rails 33 are actuated in accordance with the rotation, and as an action/effect thereof, the first member 2 and the second member 3 slide rectilinearly.

Preferably, each base portion 31 of the second member 3 has a stopper 34 provided at an end portion at the side in the longitudinal direction at which a fixing needle 32 is provided. If the rectilinear cog rails 33 are provided on the side surfaces of the base portions 31, the stoppers 34 are preferably provided at the end portions of the cog rails 33.

By providing the stoppers 34, the movement (sliding) of the first member 2 with respect to the second member 3 as a reference is restricted so that the drill bodies 22 can be prevented from advancing excessively in the direction of the fixing needles 32 and cutting of the jawbone 4 more than necessary can thereby be prevented.

A positional relationship of the stoppers 34 and the drill bodies 22 shall now be described in detail. The stoppers 34 are preferably provided at positions such that the tip portions 22a of the drill bodies 22 are restricted from moving beyond axes or extension lines of axes of the fixing needles 32. The drill bodies 22 can thereby be prevented from advancing excessively in the direction of the fixing needles 32 and cutting of the jawbone 4 more than necessary can thereby be prevented.

As shown in FIGS. 1, 2, and 4, the stoppers 34 may be provided at side surfaces of the base portions 31 that are at the rear side with respect to the side at which the fixing needles 32 are provided. In FIGS. 1 and 2, the end portions of the cog rails 33 are of modes that project in a direction opposite the direction in which the fixing needles 32 are provided and further project in directions perpendicular to the direction of projection to be provided as substantially T-shaped portions. In FIG. 4, the end portions of the cog rails 33 are of modes that simply project in the direction opposite the direction in which the fixing needles 32 are provided. The projecting portions (stoppers 34) restrain the engagement of the gears 26 and the cog rails 34 or cannot be inserted into the insertion hole 25 and thus provide an arrangement with which the first member 3 cannot slide downward any further and the downward movement of the drill bodies 22 can also be restricted.

Although the embodiment shown in FIGS. 1 to 4 is of a mode where two each of the drill bodies 22 and fixing needles 32 are provided, the present invention is not restricted thereto, and it suffices that there be at least one each of the drill body 22 and fixing needle 32.

Also the mode shown in FIGS. 1 to 4 may have an arrangement where the first member 2 and the second member 3 are capable of being split along the respective longitudinal directions, and the split first members 2 may be arranged so that each is provided with a single drill body 22 and the split second members 3 may be arranged so that each is provided with a single fixing needle 32.

An arrangement for mounting the first member 2 and the second member 3 shall now be described.

As shown in FIG. 1, etc., the first member 2 and the second member 3 are arranged to be mounted intersectingly at a predetermined angle so as to be slid-able.

The embodiment shown in FIGS. 1 to 4 has the arrangement where the base portions 31 of the second member 3 are inserted into the insertion holes 25 provided in the first member 2 to mount the two members intersectingly. The present embodiment has the arrangement where, at the part of intersection, the first member 2 is provided with the gears 26 and the second member 3 is provided with the rectilinear cog rails 33. By this arrangement, the first member 2 and the second member 3 are enabled to slide rectilinearly. Also, the gears 26 are provided with the operating portions 27 that are connected thereto, and when the operating portions 27 are rotated manually, the gears 26 rotate, the rotational force is converted to a rectilinear movement by the rack-and-pinion structure described above, and the first member 2 and the second member 3 are thus made capable of sliding while maintaining the angle of intersection.

The angle at which the first member 2 and the second member 3 intersect, that is, the angle formed by the axial direction X of the first member and the axial direction Y of the second member is not restricted. For example, the members may be intersected to form an angle of 90 degrees as shown in FIG. 1 or 4.

If the angle formed by the axial direction X of the first member and the axial direction Y of the second member is 90 degrees, an angle θ formed by boring directions of two holes 41 and 42 bored in the jawbone 4 is 90 degrees. Also, if the angle formed by the axial direction X of the first member and the axial direction Y of the second member is 120 degrees, the angle θ formed by the boring directions of two holes 41 and 42 bored in the jawbone 4 is 60 degrees.

This is calculable from the sum of the interior angles of a quadrilateral being 360 degrees. The axial direction X of the first member and the direction of the drill bodies 22 are orthogonal and the axial direction Y of the second member and the direction of the fixing needles 32 are orthogonal and in each case, an angle of 90 degrees is formed. From this, for example, if the angle formed by the axial direction X of the first member and the axial direction Y of the second member is 90 degrees, 90+90+90+θ (the angle formed by the boring directions of two holes 41 and 42 bored in the jawbone 4, the same applies hereinafter)=360, and therefore θ can be calculated as θ=90 degrees. Also for example, if the angle formed by the axial direction X of the first member and the axial direction Y of the second member is 120 degrees, 120+90+90+θ=360, and therefore θ can be calculated as θ=60 degrees.

An interval between two holes 41 and 42 bored in the jawbone 4 may be adjusted by changing the lengths of the base portion 21 of the first member 2 and a base portion 31 of the second member, that is, to be detailed, by changing the distance of a drill body 22 or a fixing needle 32 from the point of intersection of the first member 2 and the second member 3.

By the intersection/sliding arrangement of the first member 2 and the second member 3, the dental drill 1 is thus made capable of boring two or more holes at an extremely close distance, with the boring directions forming a predetermined angle with respect to a direction of growth of a natural tooth as a reference and at a predetermined interval.

The first member 2 and the second member 3 are preferably of an arrangement enabling detachment and attachment. Detachment and attachment are made possible by removing and inserting the base portions 31 of the second member 3 from and into the insertion holes 25 of the first member 2.

A method of use of the dental drill 1 shall now be described.

The dental drill 1 is a drill for boring, in the jawbone 4, a plurality of holes with which the boring directions face each other at a predetermined angle with respect to the natural tooth growing direction as a reference. Here, procedures for boring a first hole 41 and a second hole 42 in the jawbone 4 shall be described.

First, the first member 2 is used and the first hole 41 is bored in the jawbone 4 by means of a drill body 22 provided on the first member 2.

In this process, the gum 5 covering the jawbone 4 may be cut in advance to expose the jawbone 4 at the part at which the hole is to be bored. Or, the drill body 22 may be made to pierce from above the gum 5 to bore the hole in the jawbone 4 with the jawbone 4 being in the state of being covered by the gum. The drill body 22 has an extremely fine diameter like an injection needle and may be made to pierce and penetrate the gum 5 until the jawbone 4 is reached and made to cut the jawbone 4 from there to bore the first hole 41.

When the first hole 41 is bored, the second member 3 may be in a state of not being mounted to (state of being removed from) the first member 2.

The first hole 41 is bored obliquely with respect to the natural tooth growing direction. The angle of boring is, for example, 45 degrees with respect to the natural tooth growing direction as a reference.

The first hole 41 is preferably bored from an inner side or an outer side toward the outer side or the inner side of a tooth row. Treatment even at a location sandwiched by teeth at the front and rear is thereby enabled and mounting of the dental implant according to the prior application in a mode of clamping the jawbone 4 from the inner side and the outer side is made possible.

Next, a fixing needle 32 of the second member 3 is inserted in the first hole 41 that has been bored. If the second member 3 was not mounted onto the first member 2, it is mounted and then the fixing needle 32 is inserted into the first hole 41. The second member 3 is thereby fixed to the jawbone 4.

Next, the second hole 42 is bored.

Figure 7:
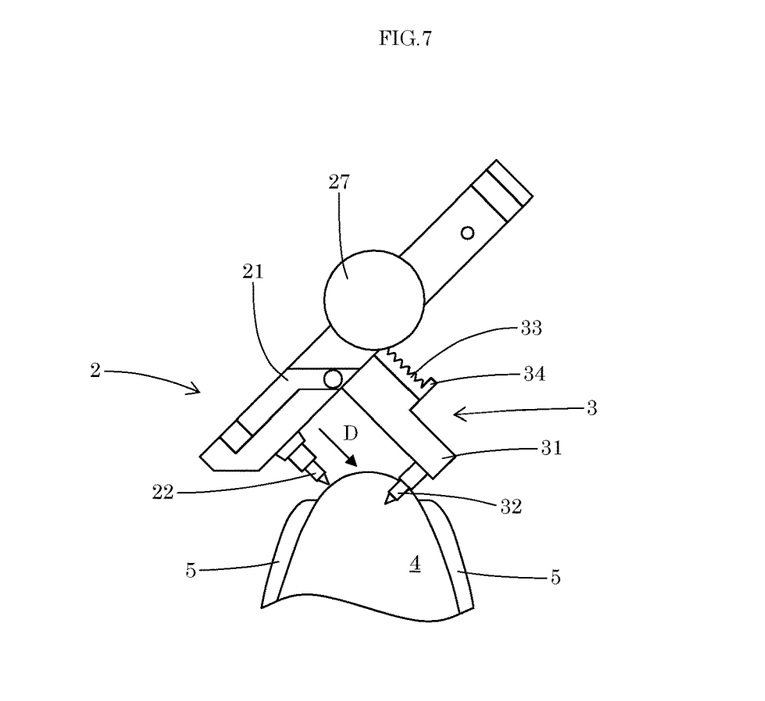
FIG. 7 is a schematic explanatory diagram of a state before a second hole is bored.

FIG. 7 shows a state where the fixing needle 32 is inserted into the first hole 41 and the second member 3 is fixed to the jawbone 4. From this state, the first member 2 is slid downward (indicates the downward direction in the figure, the same applies hereinafter) with respect to the second member 3 as a reference to move the drill body 22 in the direction of an arrow D and make it approach the jawbone 4. To slide the first member 2 downward and move the drill body 22 in the direction of the arrow D, the operating portion 27 is rotated.

Figure 8:
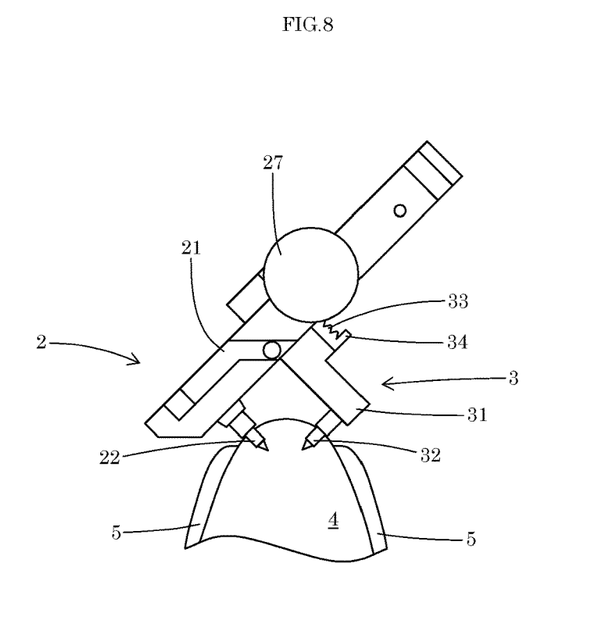
FIG. 8 is a schematic explanatory diagram of a state after the second hole has been bored.

By sliding the first member 2 downward further, the drill body 22 is made to reach the jawbone 4 so that the second hole 42 can be bored. FIG. 8 shows a state where the drill body 22 has been moved in the direction of the arrow D shown in FIG. 7 and the second bore 42 has been bored in the jawbone 4.

In this process, the sliding of the first member 2 downward is restrained by the stopper 34 contacting the first member 2. The second hole 42 is thereby prevented from being cut deeper than necessary.

By the above means, the first hole 41 and the second hole 42 can be bored with which the boring directions face each other at a predetermined angle with respect to the natural tooth growing direction as a reference.

Thereafter, the fixing needle 32 may be inserted into the second hole 42 to bore a third hole, and three or more holes can be bored in the jawbone 4 by this procedure.

The embodiment shown in FIGS. 1 and 2 has the arrangement where two drill bodies 22 are provided in parallel on the first member 2 and therefore two each of the first holes 41 and the second holes 42 are bored.

Figure 9:
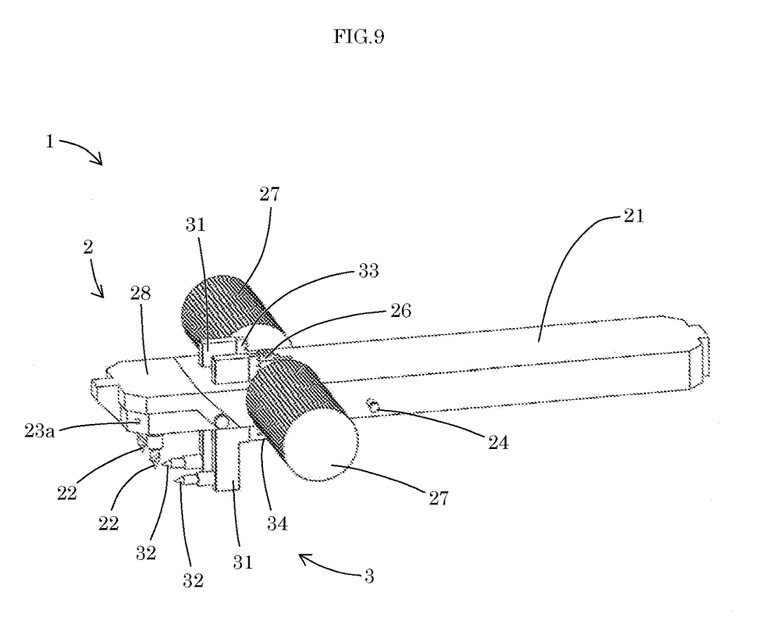
FIG. 9 is a perspective view of another embodiment of the present invention.
Figure 10:
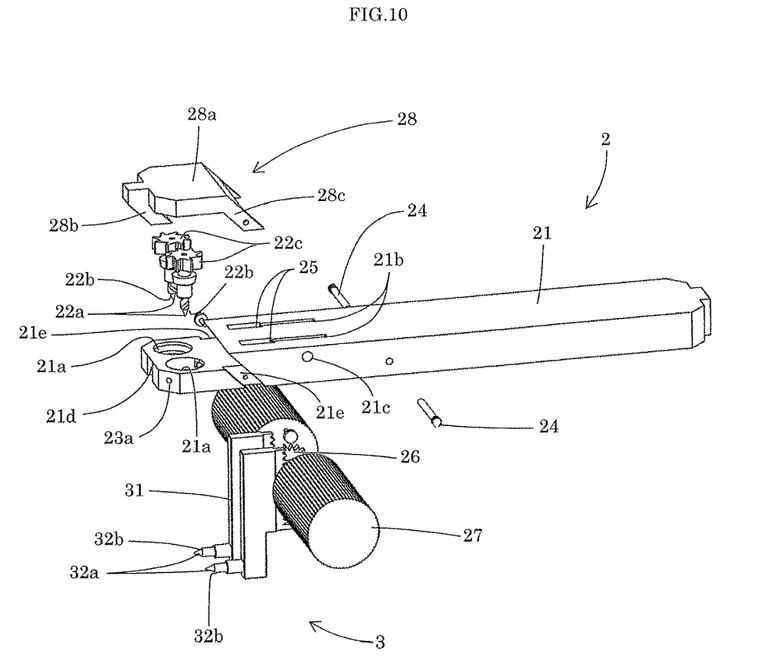
FIG. 10 is an exploded perspective view of the other embodiment of the dental drill.

Another embodiment, with which a portion of the arrangement differs from that of FIG. 1 and FIG. 2, etc., is shown in FIG. 9 and FIG. 10.

FIG. 9 is a perspective view of the other embodiment of the dental drill 1, and FIG. 10 is an exploded perspective view of the other embodiment of the dental drill 1 shown in FIG. 9.

The dental drill 1 shown in FIG. 9 and FIG. 10 has an arrangement where the base portion 21 of the first member 2 is made longer than that of the embodiment shown in FIG. 1, etc. With the present arrangement, a user, such as a dentist, etc., can perform a process while firmly gripping the base portion 21 that has been made long and can therefore perform fine control of the movement of the drill bodies 22 provided at the tip and also perform stoppage at a predetermined position easily and thus perform a rapid and precise process.

With the dental drill 1 shown in FIG. 9 and FIG. 10, the positions at which the exhaust holes 23a of the air flow passages 23 are provided differ from those of the embodiment shown in FIG. 1, etc. That is, the embodiment shown in FIG. 1, etc., has an arrangement where the exhaust holes 23a are opened in directions of being adjacent to the lid portion 28a of the drill fixing portion 28 and the exhaust holes 23a are positioned at upper sides of the height positions of the drill body housing portions 21a as shown particularly in FIG. 2. On the other hand, the other embodiment shown in FIG. 9 and FIG. 10 has an arrangement where the exhaust holes 23a not opened in the directions of the lid portion 28a of the drill fixing portion 28 but holes are bored from side surfaces of the base portion 21. With this arrangement, the exhaust holes 23a are positioned further below than centers of the height positions of the drill body housing portions 21a.

With the arrangement where the exhaust holes 23a are positioned at upper sides of the height positions of the drill body housing portions 21a, the flow of air inside each drill body housing portion 21a concentrates at the upper side and axial wobbling of the drill body 22 may occur due to the rotary vane 22c of the drill body 22 being rotated by the flow of air at the upper side. On the other hand, with the arrangement where the exhaust holes 23a are positioned further below than the centers of the height positions of the drill body housing portions 21a as shown in FIG. 9 and FIG. 10, the flow of air in each drill body housing portion 21a is not biased at the upper side and axial wobbling of the drill body 22 can be prevented.

With the dental drill 1 shown in FIG. 9 and FIG. 10, a non-slip structure is provided by means of recessed and projecting lines along a circumference of each operating portion 27. A user can thereby be suppressed from performing an erroneous operation due to slipping of the fingers when operating the operating portions 27.

The present invention is favorable for use in boring holes for implanting an implant body in a jawbone in a dental implant treatment.

DESCRIPTION OF THE SYMBOLS

1: Drills for dentistry
2: First member
21: Base portion
21a: Drill body housing portion
21b: Gear installation hole
21c: Operating portion installation hole
21d: Tip recessed portion
21e: Side surface recessed portion
22: Drill body
22a: Tip portion
22b: Step portion
22c: Rotary vane
22d: Bearing
22e: Spring
22f: Overhanging portion
22g: Disc portion
22h: Drill blade
23: Air flow passage
23a: Exhaust hole
24: Air regulating valve
25: Insertion hole
26: Gear (pinion)
27: Operating portion
27a: Shaft body
28: Drill fixing portion 28a: Lid portion
28b: Tip leg portion
28c: Side surface leg portion
28d: Fixing screw
3: Second member
31: Base portion
32: Fixing needle
32a: Tip portion
32b: Step portion
33: Rectilinear cog rail (rack)
34: Stopper
4: Jawbone
41: First hole
42: Second hole
5: Gums
A: Air flow
X: Axial direction of first member
Y: Axial direction of second member
D: Movement direction of drill body
P: Air supply source

What is claimed is:

1. A dental drill for boring a hole in a jawbone, the dental drill comprising:
   a first member having an airflow passage, said airflow passage having an air regulating valve variably restricting an airflow through said airflow passage;
   a second member intersecting slidably with said first member at a predetermined angle;
   a first drill body capable of boring a hole in a jawbone, said drill body being at one end of said first member and having an air turbine structure connectable to an air supply source via said airflow passage;
   a first fixing needle being mounted on said second member and extending in a direction perpendicular to an axial direction of said second member, said fixing needle having a tip facing in a direction of said drill body;
   whereby, said drill body bores a first hole that is bored obliquely with respect to a growth direction of a natural tooth and bores a second hole facing the first hole at a predetermined angle to the first hole;
   whereby, the second hole is bored by said drill body upon inserting said fixing needle in the first hole to fix the second member to the jawbone and by sliding said first member with respect to said second member that is fixed to the jawbone as a reference; and
   whereby the first and second holes are bored in boring directions facing each other at a predetermined angle to the growth direction of a natural tooth.

2. A dental drill according to claim 1 wherein
said drill body is arranged to bore the first hole obliquely from an inner side toward an outer side or from the outer side to the inner side of a tooth row and to bore the second hole obliquely and oppositely of the first hole from the outer side toward the inner side or from the inner side toward the outer side of the tooth row.

3. A dental drill according to claim 1 wherein
said first member comprises a gear and an operating portion coupled to said gear; and
an axial direction side surface of said second member comprises a rectilinear cog rail, said gear and said rectilinear log rail being engaged such that upon rotation of said gear said first member and said second member slide rectilinearly relative to one another.

4. A dental drill according to claim 3 wherein
said rectilinear cog rail on said second member comprises a stopper at an end portion of said rectilinear cog rail on a side of said second member where said fixing needle is arranged.

5. A dental drill according to claim 1 wherein
each of said drill body and said fixing needle comprises a step portion between a tip portion and another portion thereof, each said tip portion having a smaller diameter than the respective other portion.

6. A dental drill according to claim 1 wherein
said first member comprises a single drill body; and
said second member comprises a single fixing needle.

7. A dental drill according to claim 1 wherein
said first member comprises a second drill body parallel to and spaced at a predetermined interval from said first drill body;
said second member comprises a second fixing needle parallel to and spaced at said predetermined interval from said first fixing needle.

\* \* \* \* \*